United States Patent [19]

Tsutsuta et al.

[11] Patent Number: 5,008,627
[45] Date of Patent: Apr. 16, 1991

[54] CONDUCTIVITY DETECTOR

[75] Inventors: Koji Tsutsuta; Kiwao Seki, both of Katsuta, Japan

[73] Assignee: Hitachi, Ltd., Tokyo, Japan

[21] Appl. No.: 420,479

[22] Filed: Oct. 12, 1989

[30] Foreign Application Priority Data

Oct. 19, 1988 [JP] Japan .................. 63-261511

[51] Int. Cl.[5] ............................................. G01N 27/02
[52] U.S. Cl. .................................... 324/444; 324/439; 324/613; 324/715
[58] Field of Search ............... 324/444, 442, 439, 438, 324/613, 715, 713; 307/542

[56] References Cited

U.S. PATENT DOCUMENTS

| | | | |
|---|---|---|---|
| 3,582,767 | 6/1971 | Brum et al. | 324/442 |
| 3,993,945 | 11/1976 | Warmoth et al. | 324/449 |
| 4,365,200 | 12/1982 | Goldsmith | 324/444 X |
| 4,751,466 | 6/1988 | Colvin et al. | 324/444 X |
| 4,808,931 | 2/1989 | Ling | 324/444 |

Primary Examiner—Kenneth Wieder
Assistant Examiner—Robert W. Mueller
Attorney, Agent, or Firm—Antonelli, Terry, Stout & Kraus

[57] ABSTRACT

A conductivity detector includes an A.C. voltage supply and control circuit for applying a pair of electrodes disposed within a cell filled with electrolyte with a predetermined A.C. voltage and a correction signal generating circuit for generating a A.C. reference signal. At an auto zero adjustment operation, an output A.C. current signal flowing through the electrolyte is detected and the A.C. current is added to the A.C. reference signal. In advance of measuring conductivity, the amplitude of the A.C. reference signal is corrected until the resultant signal of the A.C. output current and the A.C. reference signal reduces to zero.

3 Claims, 2 Drawing Sheets

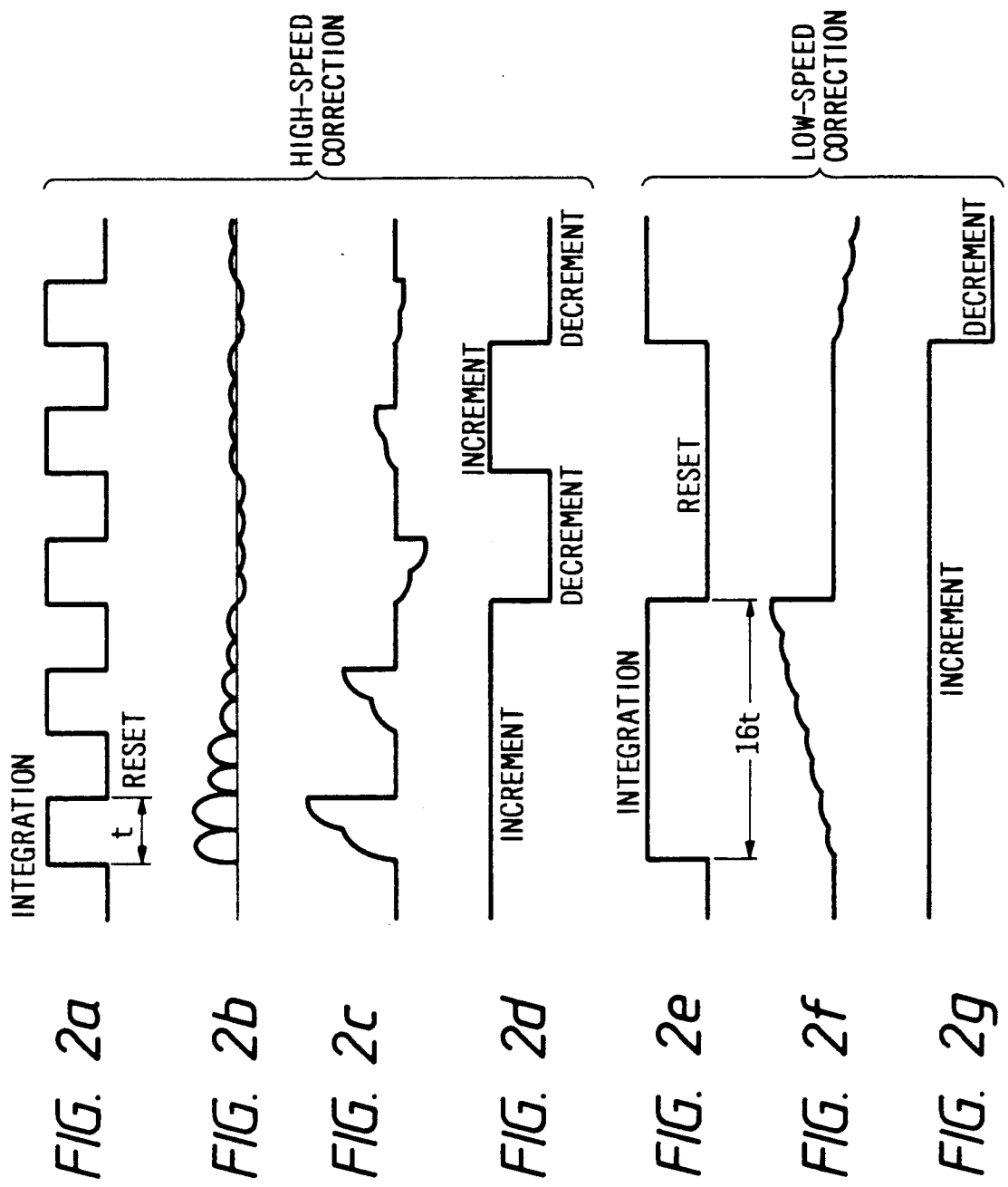

CONDUCTIVITY DETECTOR

FIELD OF THE INVENTION

The present invention relates to a conductivity detector having a control circuit suitable or eliminating a background noise with high speed and high accuracy during measuring of conductivity.

BACKGROUND OF THE INVENTION

As shown in the Japanese laying-open patent publication sho No. 62-167456(1987), the well known conductivity detector has two kinds of correction methods for compensating background noise of elute. One method performs correction of A.C. signal at input stage and the other correction of D.C. signal after rectification stage. In the correction operation, the D.C. signal correction is carried out at first, and if the background noise level is too high to be eliminated, the A.C. signal correction is performed until the noise level becomes low enough to be eliminated by D.C. signal correction.

Owing to the time delay of the rectifying circuit, the above prior art has a time difference between the correction signal for eliminating the background noise and a zero detection signal for judging completion of the correction operation. Accordingly, it requires a lot of time to repeat the correction process until the background noise becomes zero.

SUMMARY OF THE INVENTION

An object of the present invention is to provide a conductivity detector capable of eliminating a background noise of elute with high speed and high accuracy without influence of the time delay of the rectifying circuit.

BRIEF DESCRIPTION OF THE DRAWINGS

FIG. 2a-2a show signal waveforms of the circuits in FIG. 1.

DETAILED EXPLANATION OF THE PREFERRED EMBODIMENT

Figure 1:
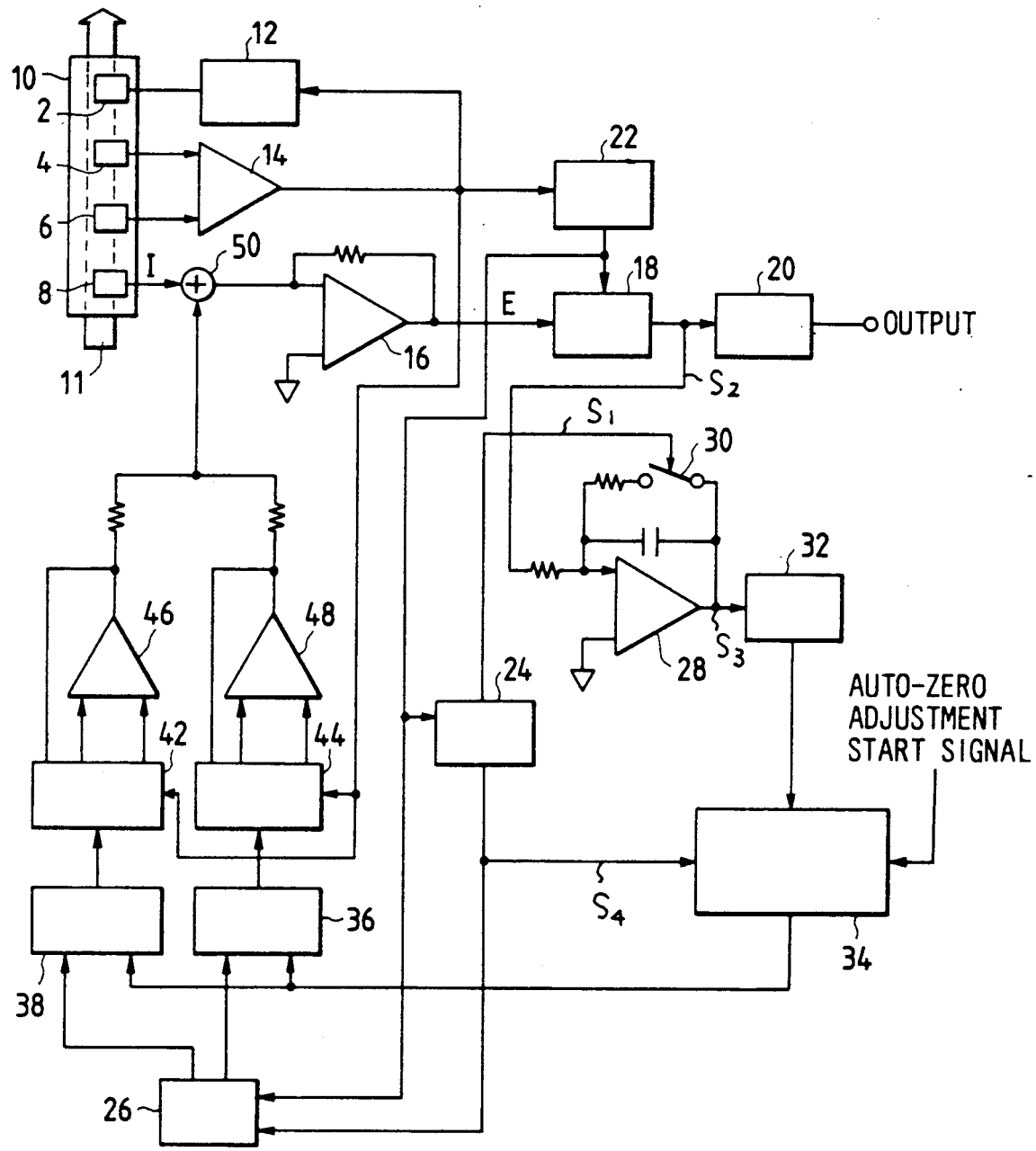
FIG. 1 is a circuit diagram of one embodiment of a conductivity detector according to the present invention.

FIG. 1 shows an embodiment of the present invention. Four electrodes 2, 4, 6, and 8 are disposed in a conductivity measuring cell 10, and electrolyte 11 to be measured conductivity flows through the cell 10. Each electrode separates by a predetermined distance from each other and electrodes 4 and 6 are positioned between the electrodes 2 and 8. An A.C. variable voltage signal is applied across the electrode 2 and the electrode 8 connected to the earth.

A variable voltage supply and control circuit 12 is controlled by an a output signal of an differential amplifier 14 so as to keep the voltage across the electrode 4 and 6 at a predetermined value. The output current I flowing from electrodes 2 to 8 through electrolyte 11 in the conductivity measuring cell 10 is changed into voltage E by a current to voltage converting circuit 16. The voltage E is changed into D.C. voltage through a synchronous rectifying circuit 18 and a smoothing circuit 20. If the voltage across the electrodes 2 and 8 keeps a predetermined value, the conductivity of the electrolyte 11 flowing through the cell 10 can be calculated on the basis of the output current I only. The output of the rectifying circuit 18 is proportional to the conductivity of the electrolyte 11 and the conductivity can be directly read out.

A synchronous signal circuit 22 supplies the synchronous rectifying circuit 18, an interval integral time control circuit 24 and a counter selection circuit 26 with a reference clock signal respectively. An integrator 28 carries out the interval integration of the synchronous rectifying signal from the rectifying circuit 18 and a reset switch 30 resets an output signal of the integrator 28. A zero detection comparator 32 judges whether the output of the interator 28 is zero or not. A counter control circuit 34 selects increment operation or decrement operation of a subordinate counter 36 and a superordinate counter 38. A starting signal for auto zero adjustment is supplied to the counter control circuit 34. The interval integral time control circuit 24 controls the reset switch 30 to change the integral time of the integrator 28.

To generate the zero adjustment signal for cancelling the backgrounding noise of elute, in addition to the counter 36, 38 a superordinate digital to analogue converter 42, a subordinate digital to analogue converter 44, a superordinate amplifier 46, a subordinate amplifier 48 are provided. This an A.C. reference sigal having a phase reverse to that of the variable A.C. signal for correcting background signal is supplied to an adder 50.

The operation of the embodiment of the present invention will be explained referring to FIG. 1 and 2. When the auto-zero adjustment start signal enters into the counter control circuit 34 at high speed adjustment, the integrator 28 integrates a synchronous rectifying signal S2 (FIG. 2b) from the synchronous rectifying circuit 18 on the basis of the interval integration time signal S1 (FIG. 2a). The integrated signal S3 (FIG. 2c) is supplied to the zero detection comparator 32. The counter control circuit 34 determines count direction, increment or decrement, of the superordinate counter 38 and the subordinate counter 36. If the output S3 of the integrator 28 is positive, the counter control circuit 34 selects increments of the counter, and to the contrary, in case the output S3 is negative, the control circuit 34 selects decrement of the counter. The increment/decrement signal S4 enters into the subordinate counter 36 or superordinate counter 38. The counting period time t(FIG. 2a) is determined by the interval integration time signal S1 from the interval integration time control circuit 24. At high speed adjustment, only the superordinate counter 38 is in counting operation. The output digital signal of the superordinate counter 38 is supplied to the superordinate digital to analogue converter 42 and as the result the correction signal is made through the superordinate amplifier 46. The correction signal is added to the A.C. current signal I by the adder 50, and the resultant signal is supplied to the integrator 28 through the current-to-voltage converting circuit 16 and the synchronous rectifying circuit 18. The zero detection comparator 32 detects whether the output signal S3 of the integrator 28 is zero or not.

The above correction operation continues until the output signal of the comparator 32 reduces to zero. To prevent the overshoot of the counter 36, 38, when each number of zero cross from positive direction or negative direction of the signal S3 becomes two, the high speed zero adjustment is stopped.

In low speed adjustment, the subordinate counter 36 is selected and the interval integration time is extended for high accuracy of the zero detection.

After completion of the high speed correction operation, the counter selection circuit 26 selects either the increment operation or the decrement operation of the subordinate counter 36 in response to the output signal of the control circuit 24. The digital output of the subordinate counter 36 is changed into an subordinate correction signal through the subordinate digital to analogue converter 44 and the subordinate amplifier 48. Both the superordinate correction signal and the subordinate signal enter into the adder 50 as the A.C. reference signal. The zero adjustment operation repeats until the output signal of the integrator 28 reduces to zero.

As shown in FIG. 2e, the interval integral time signal S1 is sixteen times as long as that of the high speed correction operation. The output signal S3 of the integrator 28 is shown in FIG. 2f. Accordingly, the counting time period of the subordinate counter 44 is sixteen times as long as that of the high speed correction operation.

When the zero cross of the output of the integrator 28 from positive direction or negative direction of the signal S3 occurs twice respectively, the low speed correction operation as well as the auto zero adjustment is completed. The data of the subordinate counter 44 and the superordinate counter 42 is maintained until the entering of the next auto zero start signal.

After the auto zero adjustment, changes of the A.C. current signal I is detected through the current-voltage converting circuit 16, the synchronous rectifying circuit 18 and the smoothing circuit 20. The D.C. output voltage indicates the real conductivity without the background noise signal of the elute.

According to the above mentioned embodiment, the response delay time is shortened to one period of the interval integral period and the zero adjustment operation is shortened because the zero detection of auto zero correction circuit is performed by the internal integral of the synchronous rectifying signal.

The superordinate counter 42 and subordinate counter 44 are used for making the zero correction signal and only the superordinate counter 42 is operated at high speed correction operation. Therefore, the time period for attaining target value of the output of the integrator is shortened.

Owing to decreasing the interval integral time at the zero adjustment, zero detection is achieved with high accuracy.

We claim:

1. An apparatus comprising:
   a cell for flowing an electrolyte;
   a pair of first electrodes disposed in said cell and separated by a predetermined distance;
   means for supplying said pair of first electrodes with a variable A.C. voltage signal;
   a pair of second electrodes disposed between said pair of first electrodes in said cell and separated by a predetermined distance for detecting the voltage across said second electrodes;
   means for controlling the output voltage of said variable A.C. voltage signal supplying means so as to maintain the voltage across said second electrodes at a predetermined value;
   means for generating a variable A.C. reference signal with reverse phase to the A.C. voltage signal;
   means for adding an output A.C. current flowing between said pair of first electrodes to the A.C. reference signal;
   means for determining whether the output of said adding means reduces to zero or not; and
   means for correcting the A.C. reference signal so as to reduce the output signal of said adding means to zero;
   wherein said zero determining means includes;
   a synchronous rectifying circuit for rectifying the output signal of said adding means;
   an interval integral circuit for performing the interval integral of the output of said synchronous rectifying circuit, and
   a comparator for determining whether the output of said interval integral circuit is zero or not, the interval integral circuit operating in synchronism with the output signal of said synchronous rectifying circuit and when the output of said interval integral circuit reduces to zero, said zero determining means determining the completion of the zero adjustment operation.

2. An apparatus according to claim 1, wherein said interval integral circuit includes:
   means for performing the interval integration at every first cycle and the zero determination; and
   means for performing the interval integration at every plural cycle of the synchronous rectifying signal and for performing the zero detection; and
   means for changing the number of the interval integration cycles.

3. An apparatus comprising:
   a cell for flowing an electrolyte;
   a pair of first electrodes disposed in said cell and separated by a predetermined distance;
   means for supplying said pair of first electrodes with a variable A.C. voltage signal;
   a pair of second electrodes disposed between said pair of first electrodes in said cell and separated by a predetermined distance for detecting the voltage across said pair of second electrodes;
   means for controlling the output voltage of said variable A.C. voltage signal supplying means so as to maintain the voltage across said pair of second electrodes at a predetermined value;
   means for generating a variable A.C. reference signal with reverse phase to the A.C. voltage signal;
   means for adding an output A.C. current flowing between said pair of first electrodes to the A.C. reference signal;
   means for determining whether the output of said adding means reduces to zero or not; and
   means for correcting the A.C. reference signal so as to reduce the output signal of said adding means to zero,
   wherein said A.C. reference signal correcting means includes superordinate and subordinate digital to analogue converters and superordinate and subordinate counters, only the subordinate counter being operated first for high speed adjustment of zero adjustment operation.

* * * * *